United States Patent
Leveen

[11] 3,972,333
[45] Aug. 3, 1976

[54] DISPOSABLE SURGICAL TOOL

[76] Inventor: Harry H. Leveen, 800 Poly Place, Brooklyn, N.Y. 11209

[22] Filed: Dec. 19, 1974

[21] Appl. No.: 534,487

Related U.S. Application Data

[62] Division of Ser. No. 337,589, March 2, 1973, abandoned.

[52] U.S. Cl. ................................. 128/318; 30/234; 128/354
[51] Int. Cl.² ................. A61B 17/32; A61B 17/30; B26B 13/00
[58] Field of Search ............ 30/234, 235, 236, 253; 128/318, 321, 354

[56] References Cited
UNITED STATES PATENTS

| 832,317 | 10/1906 | Hinds | 81/43 |
|---|---|---|---|
| 1,732,252 | 10/1929 | Blue | 30/235 X |
| 2,232,315 | 2/1941 | Craig | 30/236 |
| 2,733,716 | 2/1956 | Roberts | 128/321 |
| 3,604,071 | 9/1971 | Reimels | 128/346 |
| 3,809,094 | 5/1974 | Cook | 128/321 |

FOREIGN PATENTS OR APPLICATIONS

| 464,132 | 4/1914 | France | 128/354 |
|---|---|---|---|
| 1,110,359 | 7/1961 | Germany | 128/354 |
| 641,398 | 6/1962 | Italy | 128/321 |

Primary Examiner—Channing L. Pace

[57] ABSTRACT

A hand operated device for manipulating a pair of relatively movable cooperating tools is disclosed, having particular utility as a disposable surgical device for operating shears, forceps, hemostats and the like. The device is preferably molded of resilient plastic material and includes a pair of juxtaposed tool holding arms which are interconnected at one set of ends by a bowed portion and which are provided with a guiding device to keep the arms aligned and to limit their parting movement.

1 Claim, 4 Drawing Figures

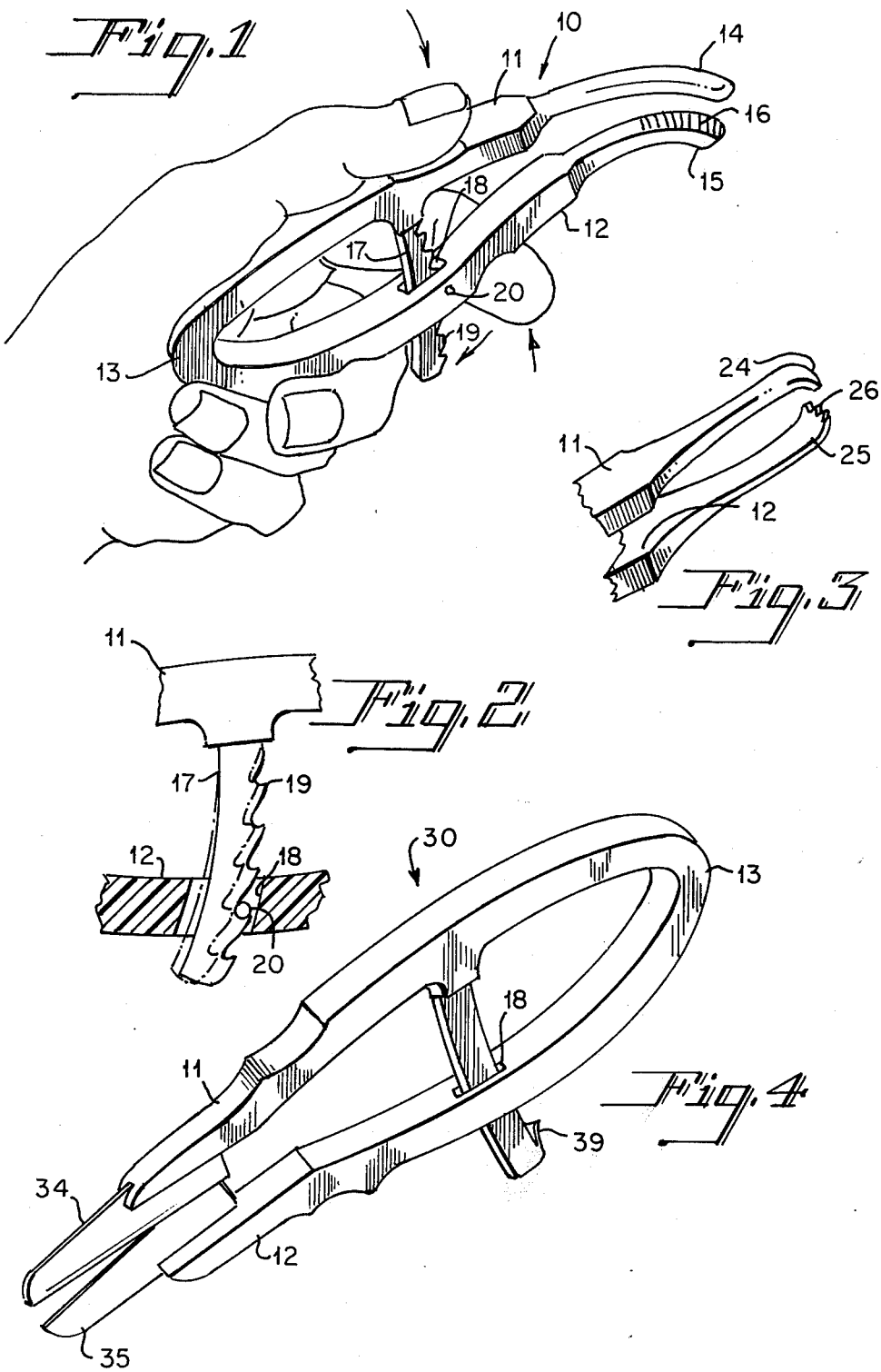

DISPOSABLE SURGICAL TOOL

This is a division of application Ser. No. 337,589, filed Mar. 2, 1973, now abandoned.

This invention relates to hand tools and in particular provides a hand operated device for manipulating relatively movable cooperating tools, such as shears, forceps and hemostats.

The present invention has for its principal object the provision of a hand operating device suitable for use by surgeons for operating cooperating tools which can be readily disposed of after use.

The desirability of disposable surgical devices is at this time well established as a convenient way of eliminating the need of sterilization prior to use in order to prevent contamination from one use to the next, since the disposable surgical tool is normally prepackaged under aseptic conditions and is disposed of after its initial use. In order for a surgical tool to be disposable it must meet certain requirements, including simplicity of manufacture and inexpensiveness of materials, simplicity of manufacture under aseptic conditions, easy manipulation and reliability in operation.

It is thus a further object of this invention to provide a disposable surgical tool meeting the above requirements.

In general it is contemplated in accordance with the present invention that a hand operated device will be provided which can be fabricated of inexpensive materials, such as the more common plastics in a simple molding operation, thus assuring its manufacture at low cost in order to render a single use of the device economic. It is further contemplated that the device will be utilized to manipulate tools operated in pairs which cooperate together to perform various operations, such as shears, forceps and hemostats. It is also contemplated that the device of this invention will have a simple construction with a minimum of engaging parts in order to permit access to all areas for sterilization. Additionally, it is contemplated that the device of this invention will be easily manipulable by grasping in the hand and squeezing in order to perform the operation of the tools reliably.

Thus, in accordance with this invention a hand operated device is provided for manipulating a pair of relatively movable cooperating tools, such as hemostats, forceps and shears, which includes a handle member formed of a pair of juxtaposed tool holding arms interconnected at one set of ends by a flexible, resilient bowed portion and carrying the cooperating tools at the other set of ends. A guiding arrangement is provided for assuring proper alignment of motion of the tool holding arms which includes a slot formed in one tool holding arm confronting the other tool holding arm and a guide arm attached at one end to the other tool holding arm and extending through the slot. A stop arrangement is provided on the guide arm for engaging the slotted tool holding arm to limit parting movement of the tool holding arms. Finally, the bowed portion is stressed in a manner to urge apart the tool holding arms.

For a more complete understanding of the practical application of this invention reference is made to the appended drawings in which:

FIG. 1 is a perspective view of a tool holding device in accordance with this invention for operating a hemostat;

FIG. 2 is an enlarged, fragmentary, partially cut away view of a portion of the device shown in FIG. 1;

FIG. 3 is a fragmentary view of a device similar to that shown in FIG. 1 modified to carry a pair of forceps; and FIG. 4 is a perspective view of a device similar to that shown in FIG. 1 for operating a pair of shearing elements.

Referring more particularly to FIGS. 1 and 2, the reference numeral 10 designates a hand operated tool in accordance with this invention generally designed for operation as a hemostat and suitable as a disposable surgical device. Tool 10 basically is composed of a pair of juxtaposed arms 11 and 12 interconnected by a bowed portion 13 at one set of adjacent ends of arms 11 and 12. Tool elements in the forms of presser fingers 14 and 15 are connected to the other set of ends of arms 11 and 12, respectively. Presser fingers 14 and 15 generally are provided with roughened confronting surfaces, as indicated at 16 on presser finger 15, such that when arms 11 and 12 are brought together such confronting surfaces apply pressure to a blood vessel or the like positioned between them to compress the vessel and close it.

Tool 10 is further provided with a guide arm 17 which is joined at one end to arm 11, on the side of arm 11 confronting arm 12, and guide arm 17 extends toward arm 12 and through an opening 18 formed through tool holding arm 12, which confronts tool holding arm 11 thereby enabling guide arm 17 to pass freely through opening 18. As can be seen better in FIG. 2, along its side facing presser fingers 14 and 15 guide arm 17 is provided with a series of ratchet teeth 19, and a pin 20 extends transversely through tool holding arm 12 across opening 18 in a position such that pin 20 engages ratchet teeth 19. The latter are inclined at their points toward arm 11, such that the engagement of teeth 19 with pin 20 restrains parting movement of arms 11 and 12 at a series of positions, but permits their movement in a direction toward each other.

It will be further observed that the lateral dimensions of guide arm 17 are not only such that guide arm 17 can move freely within opening 18, but are also such that guide arm 17 can be moved away from pin 20 to disengage ratchet teeth 19, thereby permitting parting movement of tool holding arms 11 and 12.

Tool 10 is manufactured in one piece in a molding operation of flexible, resilient plastic material, such as polyethylene, polypropylene, polyvinylchloride or the like. In the molding operation pin 20, which is preferably formed of stainless steel or the like, is introduced in the mold as an insert, such that tool holding arm 12 is molded about it to retain it. Also in the molding operation tool holding arms 11 and 12 are formed at a substantial angle to each other, such that guide arm 17 lies wholly between them and does not enter opening 18. Thus, before use, tool holding arms 11 and 12 are moved together by pressure to insert guide arm 17 into opening 18 and to engage one or more ratchet teeth 19 with pin 20. Thus at all times afterward bowed portion 13 of tool 10 is under substantial internal stress tending to urge apart tool holding arms 11 and 12.

In use tool 10 is grasped in the hand, substantially as shown in FIG. 1, and presser fingers 14 and 15 are applied about the blood vessel or other object to be clamped. Pressure is then applied between the thumb and forefinger to urge together tool holding arms 11 and 12 bringing presser fingers 14 and 15 into clamping cooperation. As this movement occurs, ratchet teeth 19 slip passed pin 20 until movement stops. When the hand pressure is released pin 20 engages a ratchet tooth 19 prevents parting movement of presser fingers 14 and 15 which remain in clamping position. When such clamping action is to be released tool 10 is grasped, as before, and the forefinger is pulled back toward guide arm 17 where this protrudes through tool holding arm 12 to move guide arm 17 to the dashed line position shown in FIG. 2, thereby releasing engagement of ratchet teeth 19 and pin 20 and permitting the built-in stress in bowed portion 13 to urge apart tool holding arms 11 and 12 and thereby remove the clamp.

Substantially the same structure can be utilized to construct a disposable pair of surgical forceps, for example, tissue grasping forceps, as shown in the fragmentary view in FIG. 3. In this arrangement presser fingers 14 and 15 are replaced by forceps 24 and 25 which have serrated confronting edges, as indicated by the reference numeral 26 on forceps 25. The construction and operation is otherwise as shown in FIGS. 1 and 2 regarding tool 10.

A modification is shown in FIG. 4 in which a surgical tool 30 suitable as a disposable surgical shear is shown. Tool 30 has generally the same construction as tool 10 and is thus provided with tool holding arms 11 and 12 and bowed portion 13 interconnecting such tool holding arms. In place of presser fingers 14 and 15, however, arms 11 and 12 are attached to a pair of stainless steel shearing blades 34 and 35, which are positioned to engage in a shearing action as arms 11 and 12 are pressed together. Opening 18 is retained in arm 12, but guide arm 17 is replaced by a guide arm 37 in which ratchet teeth 19 are eliminated. Guide arm 37 at its end remote from tool holding arm 11 is provided with a detent 39 along its side directed toward bowed portion 13 of tool 30.

In construction tool 30 is molded like tool 10 with tool holding arms 11 and 12 spread apart at a substantial angle, such that guide arm 37 lies wholly between tool holding arms 11 and 12. Blades 34 and 35 are used as inserts in the mold, such that tool holding arms 11 and 12, respectively, are molded about them. Detent 39 is formed as a thin, flexible tab on the end of guide arm 37 and is inclined toward tool holding arm 11. Thus when guide arm 37 is inserted into opening 18, as tool holding arms 11 and 12 are pressed together, detent 39 retracts toward guide arm 37 to pass through opening 18 after which it snaps open to prevent withdrawal of guide arm 37 from opening 18. Ideally the location of detent 39 is such that when it bears against the underside of tool holding arm 12, after having been pressed through opening 18, shearing blades 34 and 35 are in an initial meshing position. Thus when tool holding arms 11 and 12 are pressed together blades 34 and 35 close together in a shearing type action which is reversed upon release of tool holding arms 11 and 12 back to the point of initial engagement in which detent 39 bears against tool holding arm 12.

I claim:

1. A hand operated device for manipulating a pair of relatively movable cooperating tools comprising a handle member including a pair of juxtaposed tool holding arms and a resilient flexible bowed portion inter-connecting said pair of tool holding arms at one set of adjacent ends thereof, guide means including means defining an opening through one said tool holding arm confronting the other said tool holding arm, a guide arm attached at one end thereof to the other said tool holding arm, the other end of said guide arm extending through said opening and stop means on said guide arm engagable with the structure of said one tool holding arm upon parting movement of said pair of tool holding arms, said bowed portion of said handle member being internally stressed whereby this other set of adjacent ends of said tool holding arms are urged apart to cause said stop means to engage said one tool holding arm wherein said stop means includes a fixed non adjustable detent on said guide arm at the terminal end thereof remote from the other said tool holding arm and a pair of shearing blades attached to the ends of said tool holding arms remote from said bowed portion of said handle in which said detent limits parting movement of said tool holding arms to the initial part of mesh of said shearing blades by bearing against the underside of said one tool holding arm after having been pressed through said opening so that the shearing blades are in an initial meshing position.

* * * * *